(12) United States Patent
Kennedy et al.

(10) Patent No.: US 10,916,349 B2
(45) Date of Patent: Feb. 9, 2021

(54) METHOD FOR DETERMINING VASCULAR ACCESS RISK IN A HEMODIALYSIS PATIENT POPULATION

(71) Applicant: Henry Ford Health System, Detroit, MI (US)

(72) Inventors: John Kennedy, Evanston, IL (US); Brad Astor, Madison, WI (US); Jeffrey J. Sands, Orlando, FL (US); Helen Kimball Hirschman, Evanston, IL (US); Douglas Curry, West Lafayette, IN (US); Stanley Frinak, Farmington Hills, MI (US); Gerard Zasuwa, West Bloomfield, MI (US); Jerry Yee, Beverly Hills, MI (US); Anatole Besarab, Bloomfield Hills, MI (US); Lalathaksha Kumbar, Troy, MI (US)

(73) Assignee: Henry Ford Health System, Detroit, MI (US)

( * ) Notice: Subject to any disclaimer, the term of this patent is extended or adjusted under 35 U.S.C. 154(b) by 0 days.

(21) Appl. No.: 16/577,574

(22) Filed: Sep. 20, 2019

(65) Prior Publication Data
US 2020/0098479 A1     Mar. 26, 2020

Related U.S. Application Data

(60) Provisional application No. 62/734,556, filed on Sep. 21, 2018.

(51) Int. Cl.
*G16H 50/30* (2018.01)
*G16H 50/70* (2018.01)
*G16H 10/60* (2018.01)

(52) U.S. Cl.
CPC ............ *G16H 50/30* (2018.01); *G16H 10/60* (2018.01); *G16H 50/70* (2018.01)

(58) Field of Classification Search
CPC ......... G16H 50/30; G16H 50/70; G16H 10/60
(Continued)

(56) References Cited

U.S. PATENT DOCUMENTS 7,597,666 B2   10/2009   Frinak et al.
8,348,850 B2   1/2013    Frinak et al.
(Continued)

FOREIGN PATENT DOCUMENTS

WO    2016164809 A1    10/2016
WO    WO-2016164809 A1 * 10/2016  ............. A61B 34/10

OTHER PUBLICATIONS

International Search Report and Written Opinion for Application No. PCT/US2019/052258, dated Jan. 10, 2020, 9 pages.

*Primary Examiner* — Joy Chng
(74) *Attorney, Agent, or Firm* — Brooks Kushman P.C.

(57) ABSTRACT

A method for determining risk of an adverse event, such as thrombosis or a required intervention, associated with a vascular access includes receiving hemodialysis treatment data associated with the vascular access, deriving a plurality of selected risk factors from the hemodialysis treatment data, evaluating the plurality of selected risk factors over a time period, assigning raw scores to each selected risk factor based on its values over the time period, summing the raw scores for the plurality of selected risk factors to determine a cumulative raw score, and correlating the cumulative raw score with a level of risk of an adverse event associated with the vascular access.

20 Claims, 6 Drawing Sheets

(58) Field of Classification Search
USPC .......................................................... 705/2–3
See application file for complete search history.

(56) References Cited

U.S. PATENT DOCUMENTS

| | | | |
|---|---|---|---|
| 8,974,394 B2 | 3/2015 | Frinak et al. | |
| 2006/0020490 A1* | 1/2006 | Staton, Jr. | G16H 50/20 705/2 |
| 2009/0303462 A1* | 12/2009 | Munger | A61B 5/0059 356/39 |
| 2012/0059779 A1* | 3/2012 | Syed | G06N 20/00 706/12 |
| 2016/0029972 A1* | 2/2016 | Lenehan | A61B 5/02108 600/301 |

* cited by examiner

METHOD FOR DETERMINING VASCULAR ACCESS RISK IN A HEMODIALYSIS PATIENT POPULATION

CROSS-REFERENCE TO RELATED APPLICATIONS

This application claims the benefit of U.S. provisional application Ser. No. 62/734,556 filed Sep. 21, 2018, the disclosure of which is hereby incorporated in its entirety by reference herein.

TECHNICAL FIELD

Embodiments relate to a method for determining risk of an adverse event associated with a vascular access, such as thrombosis or a required intervention.

BACKGROUND

Patients who lose the use of their kidneys must undergo hemodialysis to remove fluids and toxins from the body. This requires the existence of a vascular access in order to remove the blood for treatment and then return it to the body. The preferred vascular access is an arteriovenous (AV) access (either an AV fistula—AVF or AV graft—AVG) created by joining an artery to a vein directly (AVF) or by interposing an artificial vessel to connect the artery to the vein (AVG). There are only a limited number of sites on the body where an AV access can be placed, so preserving these sites is critical. Unfortunately, stenosis (growth of a lesion inside the vessel wall) may develop over time and can lead to a thrombosis. The procedures used to reopen a thrombosed access are invasive, and even if successful this procedure can cause damage to the access which may shorten its life. There are elective interventional procedures that can mitigate the onset of stenosis, but knowing when to refer a patient for these preventive procedures has been a challenge.

SUMMARY

In one or more embodiments, a method for determining risk of an adverse event associated with a vascular access includes receiving hemodialysis treatment data associated with the vascular access, deriving a plurality of selected risk factors from the hemodialysis treatment data, evaluating the plurality of selected risk factors over a time period, assigning raw scores to each selected risk factor based on its values over the time period, summing the raw scores for the plurality of selected risk factors to determine a cumulative raw score, and correlating the cumulative raw score with a level of risk of an adverse event associated with the vascular access.

In one or more embodiments, a method for determining risk of an adverse event associated with a vascular access includes evaluating hemodialysis treatment data associated with the vascular access to derive a plurality of selected risk factors relating to venous access pressure ration (VAPR), arterial access pressure ratio (AAPR) and blood flow rate, evaluating the plurality of selected risk factors over a time period, assigning raw scores to each selected risk factor based on its values over the time period, summing the raw scores for the plurality of selected risk factors to determine a cumulative raw score, and correlating the cumulative raw score with a final risk score indicative of a probability of an adverse event associated with the vascular access.

In one or more embodiments, a method for determining risk of thrombosis or a required intervention associated with a vascular access includes receiving hemodialysis treatment data associated with the vascular access, deriving a plurality of selected risk factors from the hemodialysis treatment data, the plurality of selected risk factors relating to VAPR, AAPR and blood flow rate, evaluating the plurality of selected risk factors over a time period to determine risk factor values including averages, slopes, and number of alerts, assigning raw scores to each selected risk factor based on its values over the time period, summing the raw scores for the plurality of selected risk factors to determine a cumulative raw score, correlating the cumulative raw score with a final risk score indicative of a probability of thrombosis or a required intervention associated with the vascular access, and prioritizing the vascular access for risk of thrombosis or a required intervention among a hemodialysis patient population.

DETAILED DESCRIPTION

Figure 1:
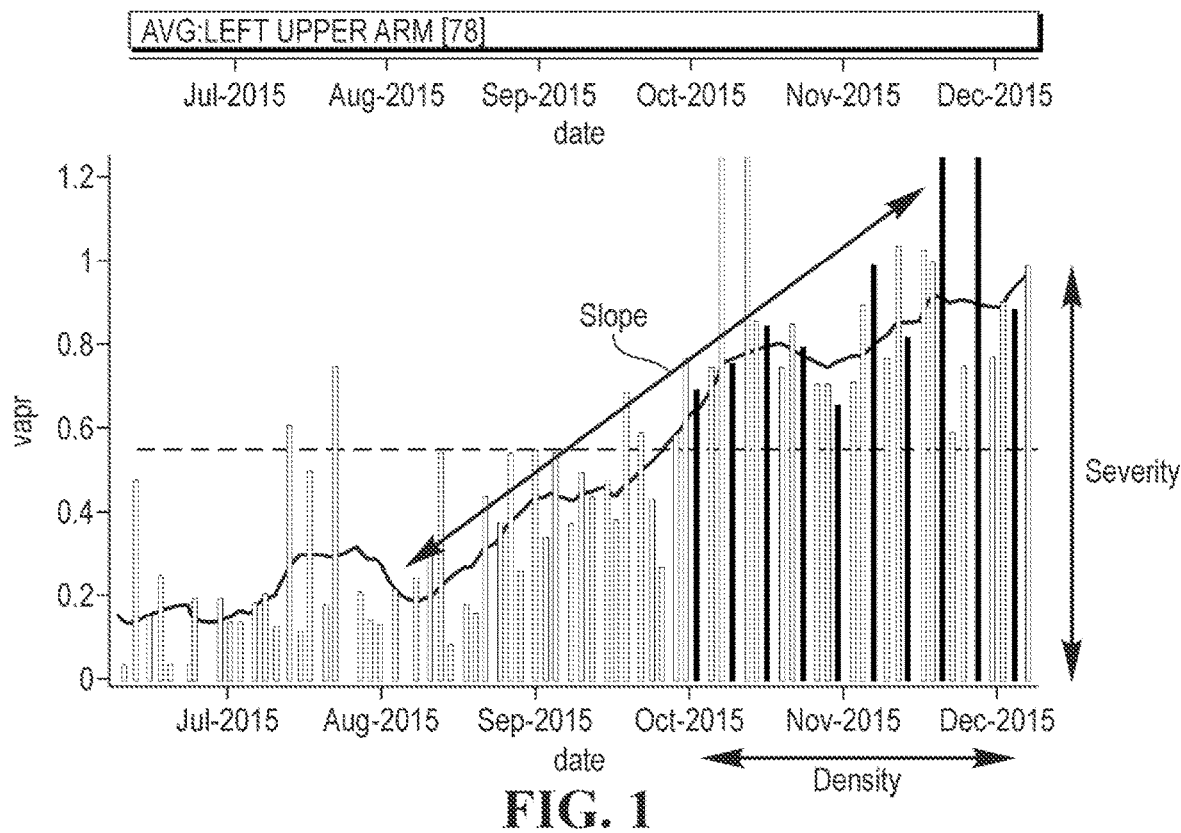
FIG. 1 is a graph of venous access pressure ratio (VAPR) in an AVG over time illustrating the factors of density (number of alerts), severity (how high is the pressure), and slope which together relate to the risk of access complications.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

As a matter of background, hemodialysis machines utilize two needles, one to remove blood from the patient (arterial) and one to put the dialyzed blood back into the patient (venous needle). During hemodialysis, blood is drawn from the vascular access through the arterial needle by the hemodialysis machine blood pump. After passage through the dialyzer, the blood traverses the venous drip chamber and returns to the access through the venous needle. The pressure required to infuse blood back into the access through the venous tubing and access needle and to overcome the pressure within the access is recorded as the venous drip chamber pressure (VDP). One component of VDP is the access pressure at the venous needle site (venous access pressure (VAP)). Another component of VDP is the combined pressure required to overcome the resistance to flow through the tubing distal to the drip chamber (low) and through the venous return needle (high). VDP is also a function of needle size, tubing length and blood viscosity, represented by hematocrit. If the venous pressure within an access at the needle site is 0 mmHg, VDP can be defined as $VDP_0$, i.e., the venous drip chamber pressure when the access pressure is zero. Consequently, $VDP_0$ can be calculated for a given hemodialysis machine, tubing set, and needle size when the blood flow rate and hematocrit are measured. Once $VDP_0$ is determined, VAP can be calculated from the measured VDP: $VAP=VDP-VDP_0$. To normalize variations in VAP attributed to changes in mean arterial pressure (MAP), the venous access pressure ratio (VAPR) is calculated: VAPR=VAP/MAP. An arterial access pressure ratio (AAPR) can be calculated in a corresponding manner.

There are many factors that should be considered by nephrologists and dialysis staff before they can decide whether to refer a patient for vascular access imaging and intervention. For example, these factors may include whether the blood flow delivered to the hemodialysis machine is steady and achieving the prescribed goals, whether the hemodialysis treatments are achieving adequate clearances for removing fluids and toxins, how many alerts (such as AAPR and/or VAPR, and delivered blood flow) have occurred in the last 30 to 60 days, how high both the arterial and venous intra-access pressures are, the rate of change in the pressures from treatment to treatment, the type of access (AVF or AVG), and the past history of the access, to name a few.

The process of considering all of these factors when evaluating a patient's risk of access complications takes time and expertise. As a result, incorrect or non-optimal treatment decisions may be made due to the time and focus required to compile and digest all of the factors for consideration. While vascular access surveillance can identify patients with AVF or AVG at high risk of having stenosis which may lead to access thrombosis, determining which patients' stenosis will cause thrombosis and the lead time to these adverse events remains less clear. This type of risk assessment is necessary to allow timely interventions for the patients in need, and to avoid unnecessary procedures for other patients.

U.S. Pat. No. 7,597,666 directed to a method of vascular access surveillance is incorporated by reference herein in its entirety. Hemodialysis treatment data is used to calculate intra-access venous (VAPR) and arterial (AAPR) pressure ratios for each treatment to identify whether a patient's vascular access is a high risk for thrombosis and needing further evaluation and/or elective intervention. In one embodiment, alerts may be generated when the VAPR>0.55 or the AAPR>0.65 for AVF or AAPR>0.60 for arteriovenous graft AVG on three consecutive treatments. However, VAPR and AAPR are only two of the many factors that can indicate risk of thrombosis or access complications.

While this method of vascular access surveillance provides a reliable signal ("alert") that a patient has an increased risk for vascular access complications, there is currently no mechanism to prioritize one patient on an alert list over another. This task has been left to nephrologists and facility staff to review, triage, and individually assess the severity of the risk to determine which patients should be referred and when this referral should take place. However, in many busy facilities this individualized approach has become impractical either due to lack of staff time or lack of expertise.

The solution lies in creating a score that can prioritize patients for risk. Accordingly, the system and method disclosed herein include a multifactorial scoring algorithm to estimate the risk of a patient developing vascular access thrombosis or undergoing an intervention, such as over a time period (e.g., within the subsequent 60 days). The method disclosed herein utilizes a selected subset of the risk factors that could be used for triaging patients at high risk for an adverse vascular access event. These risk factors may include a) the number of VAPR and AAPR alerts, b) the average normalized VAPR, c) the average normalized AAPR, d) the slope of the average normalized venous pressure (VAPR) over time, e) the number of hemodialysis treatments that do not achieve at least 90% of the prescribed blood flow, and f) the location of the access. Other known risk factors for access dysfunction can also be included, such as the slopes of the averaged normalized arterial pressure (AAPR) over time, and the past history of interventions performed on a specific access.

By combining the results of these risk factors into a numeric 'score', problems with the vascular access may be better anticipated in advance based on these individualized patient-related factors. By providing an early indication of increased risk for an adverse event, sufficient lead time may be provided to allow time to schedule the patient for a proactive intervention. By combining these risk factors and their relative weighting (raw scores) for access complications into a simple score, clinical staff is provided with a way to optimize the prioritization process of selecting patients in need of having their vascular access examined for possible intervention.

There are several quantifiable factors that relate to the risk of access complications, and FIG. 1 illustrates three of these risk factors. Density is the number of VAPR or AAPR alerts (pressure threshold exceeded) in a given time period, where more alerts indicate a higher risk. In the scoring method disclosed herein, different time periods may be given different weights, such that more recent results may carry more weight than prior results. Severity is the relative pressure (AAPR, VAPR) in the access during a given time period, where generally the higher the average pressure, the higher the risk. Similarly, an increasing or declining VAPR and/or AAPR may also indicate progressive stenosis with declining access blood flow. Slope is the increasing (or decreasing) pressure over time and may indicate how fast an occlusion is growing, where the faster the growth, the higher the risk. For example, slope may be calculated from the difference between the average VAPR of the most recent time period compared with a prior time period, or it may be derived by performing a regression over a given time period. In the disclosed scoring method, a steep slope may be weighted greater than a gradual climb.

Additional known risk factors may also be included in the scoring algorithm. For example, hemodialysis machine blood flow can be evaluated to determine if the prescribed blood flow rate been achieved in recent treatments. The more treatments not achieving adequate and/or prescribed blood flow rate, the higher the risk. The percentage of the prescribed blood flow actually being achieved can be assessed, such as, but not limited to, the number of treatments in a prior period where the average blood flow in a treatment session was less than, for example, 90% of the prescribed blood flow. This factor may be weighted greater for those patients who have missed the prescribed blood flow by a higher percentage.

There are many risk factors that could be included in the scoring system and method disclosed herein. For example, the AV access type and location can be included as risk factors. Patients may be using either an AVF or an AVG access, and it may be important to keep these types of accesses separate since they have very different characteristics. AVG accesses tend to have more complications than AVF accesses but are easier to repair, where AVF accesses are less prone to complications but are harder to return to patency. Access location may also have an impact on the results and may be considered during interpretation. In addition, the history of interventions to correct complications in the patient's access can be included as a risk factor, as one or more prior interventions may increase the risk of access complications going forward. Additionally, other clinical variables such as age, gender, body weight, blood pressure, diabetic status, etc. may be associated with increased risk and can be included as risk factors. The risk factors disclosed herein are not intended to be an exhaustive list, and it is understood that other commonly collected values are also contemplated.

Taken together, at least some of these variables can form the basis of a system and method that prioritize the patients on an alert list, and a scoring framework utilizing these variables can predict patients who are at high risk for a thrombosis event or requiring intervention. In this way, many variables can be combined into a simple risk score that the patients, physicians and medical staff can refer to as an indicator of risk, where the score should correlate with the risk of a thrombosis and increase as the vascular access becomes more occluded.

To develop the algorithm, time periods prior to a thrombotic or documented intervention event were analyzed. In one example, 15, 30, 60, 90, and 120 days prior to an intervention can be selected. As an example of a practical time period, approximately 15 days may be required for staff to react to an indication of high risk and have a reasonable chance of securing an intervention before the thrombosis event. A 15-day time point also enables capturing data for a patient that has a rapidly growing stenosis. Of course, other time periods are also possible.

In one study, 985 patients (263 AVF; 722 AVG) were identified, including 304 (81 AVF, 223 AVG) who experienced vascular access thrombosis and 681 (182 AVF, 499 AVG) without thrombosis, from 86 hemodialysis facilities with electronic download of treatment and vascular access intervention data with up to 120 days of treatment data per patient. Records were divided into 15-day intervals (total intervals=7655; 2049 AVF and 5606 AVG) and assessed to determine outcome (thrombosis vs. no thrombosis) within the subsequent 60 days.

Sequential multivariant regression along with the use of cubic splines that allows for non-linearity identified a plurality of risk factors significantly associated ($p<0.05$) with access thrombosis or an angioplasty intervention procedure in AVF and AVG within 60 days: mean AAPR over 28 days, mean VAPR over 28 days (severity), VAPR slope (change/28 days), number of VAPR alerts over 28 days (density), and the number of treatments where delivered/prescribed blood flow rate <90% over 28 days (adequacy). In one or more embodiments, each risk factor has a possible raw score range based on the predictive value of the risk factor for thrombosis or intervention. For example, score ranges for an AVF could include 0-8 for mean AAPR, 0-8 for VAPR slope, 0-3 for treatment blood flow rates <90% prescribed, 0-2 for number of VAPR alerts, and 0-12 for mean VAPR. Within the possible score range for each risk factor, a raw score may be assigned for each factor based on its value over a time period. The raw scores for all of the risk factors may then be summed to obtain a cumulative raw score. The cumulative raw score may be categorized based on the type or location of the access (for example, an AVF in the upper arm or the lower arm) or other factors. The resulting cumulative raw score may then be associated with a level of risk, such as a final risk score (for example, ranging from 1-10), where the higher the number, the higher the risk of a thrombosis or intervention.

Figure 2:
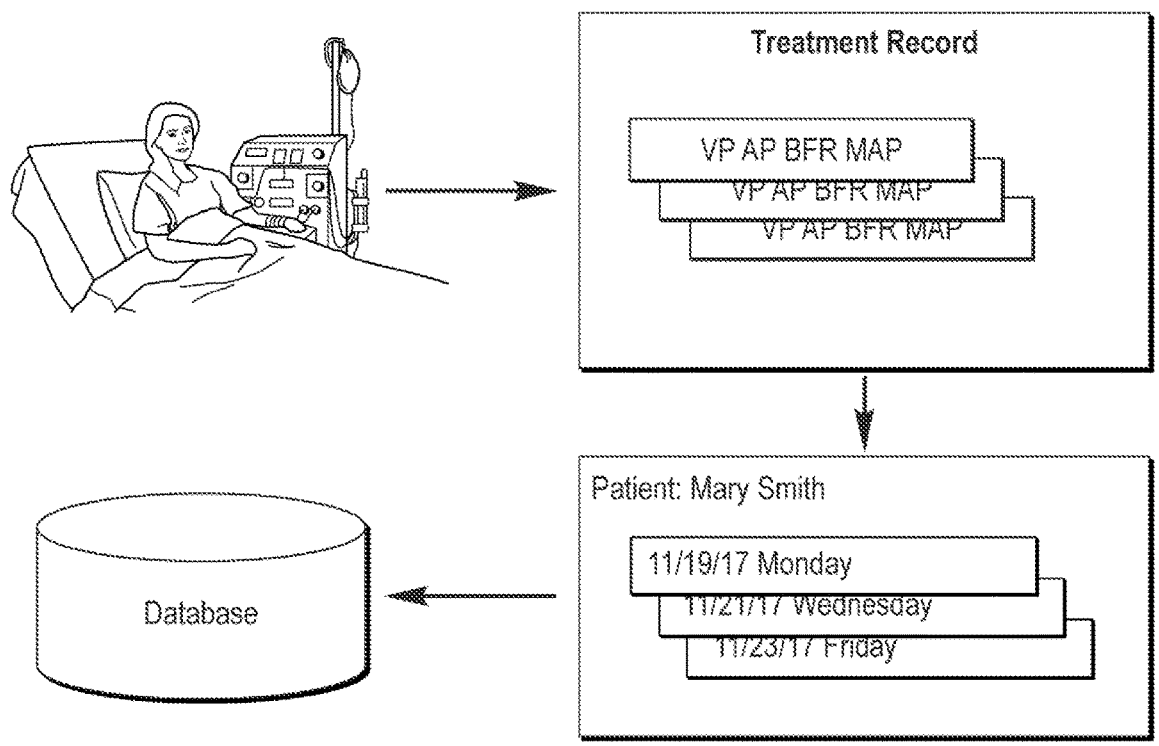
FIG. 2 is a schematic illustration of data obtained during a hemodialysis treatment session for a patient, wherein data for a plurality of treatment sessions may be stored in a database.
Figure 3:
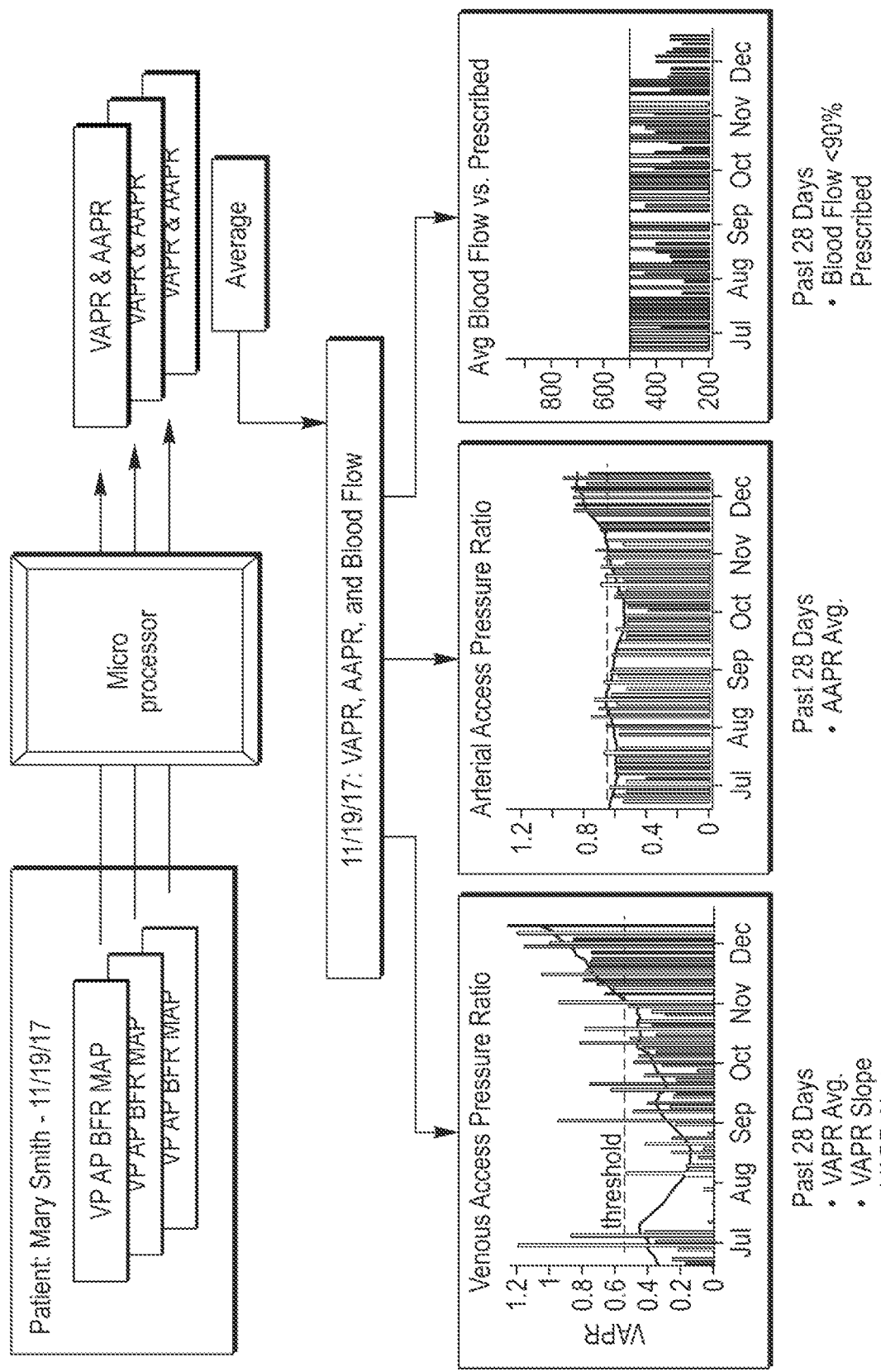
FIG. 3 is a schematic illustration of calculating risk factors such as VAPR, arterial access pressure ratio (AAPR), and blood flow from the hemodialysis treatment data, and then evaluating these risk factors over time to determine, for example, average VAPR, VAPR slope, number of VAPR alerts, average AAPR, and blood flow <90% prescribed.

FIG. 2 is a schematic illustration of data obtained during a hemodialysis treatment session for a patient, wherein data for a plurality of treatment sessions may be stored in a database. FIG. 3 is a schematic illustration of calculating risk factors such as VAPR, AAPR, and blood flow rate from the hemodialysis treatment data, and then evaluating these risk factors over time to determine, for example, average VAPR, VAPR slope, number of VAPR alerts, average AAPR, and blood flow rate <90% prescribed.

In one or more embodiments, a system associated with the scoring method may include or be in communication with a detection device, such as a hemodialysis machine, that is able to obtain hemodialysis treatment data. The system may further include a computer-driven analyzer or microprocessor arranged to receive hemodialysis treatment data, such as from a hemodialysis machine, during and after hemodialysis. In one or more embodiments, the hemodialysis treatment data includes venous pressure (VP), arterial pressure (AP), blood flow rate (BFR), and mean arterial pressure (MAP). The computer-driven analyzer or microprocessor may include an algorithm, wherein the algorithm may be used as part of an integrated circuit. The algorithm may analyze the treatment data over time to identify patients at risk for access dysfunction, either for thrombosis or intervention, such as percutaneous transluminal angioplasty or surgery to maintain access patency. The system may also contain or be in communication with a computer database to recall individual patient information and to store hemodialysis treatment data in the patient's database record.

The findings from the regression models were used to assign raw scores indicative of risk. In one analysis, using mean AAPR as an example, intervals with a mean AAPR level for an AVF below 0.35 or above 0.525 were shown to be more likely to have a thrombosis or an intervention within 60 days compared with those with a mean AAPR between 0.35-0.525. Similar analyses were performed for each parameter. Both low and high AAPR and VAPR slope, increasing or decreasing, were shown to be associated with thrombosis or an angioplasty intervention, as progressive stenosis produces an increase or decrease in the observed intra-access pressure depending on needle/lesion position.

The specific cut-offs between categories and raw scores assigned were identified by considering the fit of the regression models and the numbers of intervals falling into each category. Any appropriate statistical modeling techniques could be applied to create the score. As described above, all of the raw scores for each of the five risk factors were added to arrive at a cumulative raw score, from which a final risk score may be determined. The probability of thrombosis or intervention was determined based on the final risk score separately for AVF upper arm location, AVF lower arm location, and AVG. For each access type/location, a higher risk score (such as from 1-10) was strongly associated with a higher probability of thrombosis or an intervention.

Figure 4:
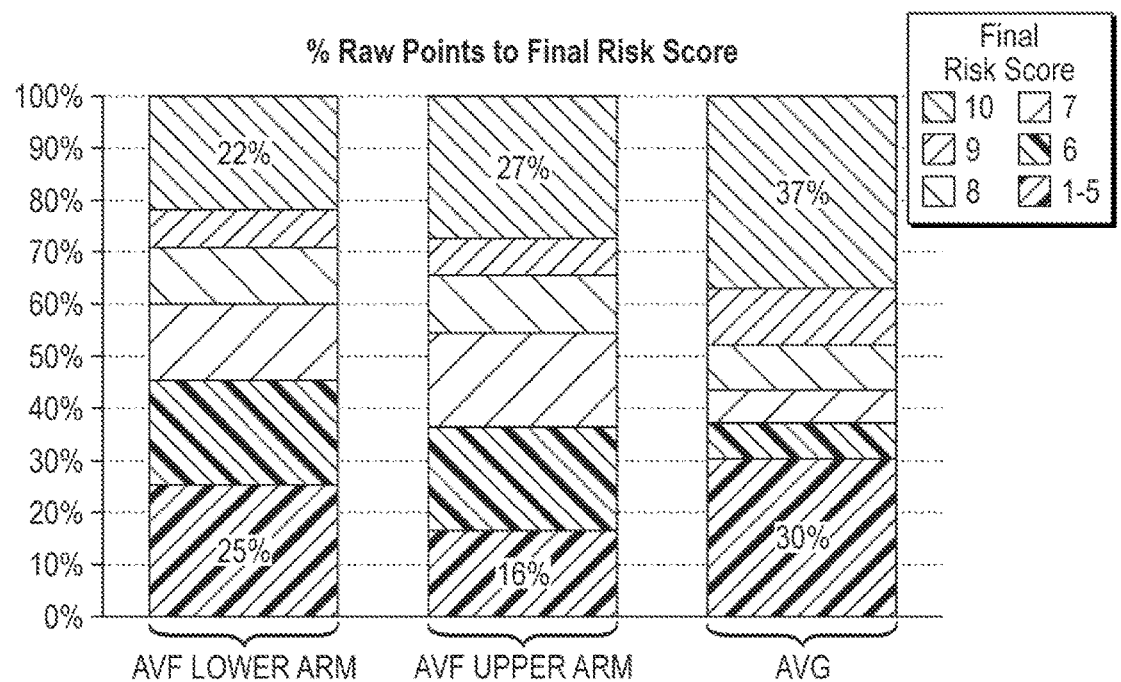
FIG. 4 is a chart illustrating the influence of vascular access location on the final risk score.
Figure 5:
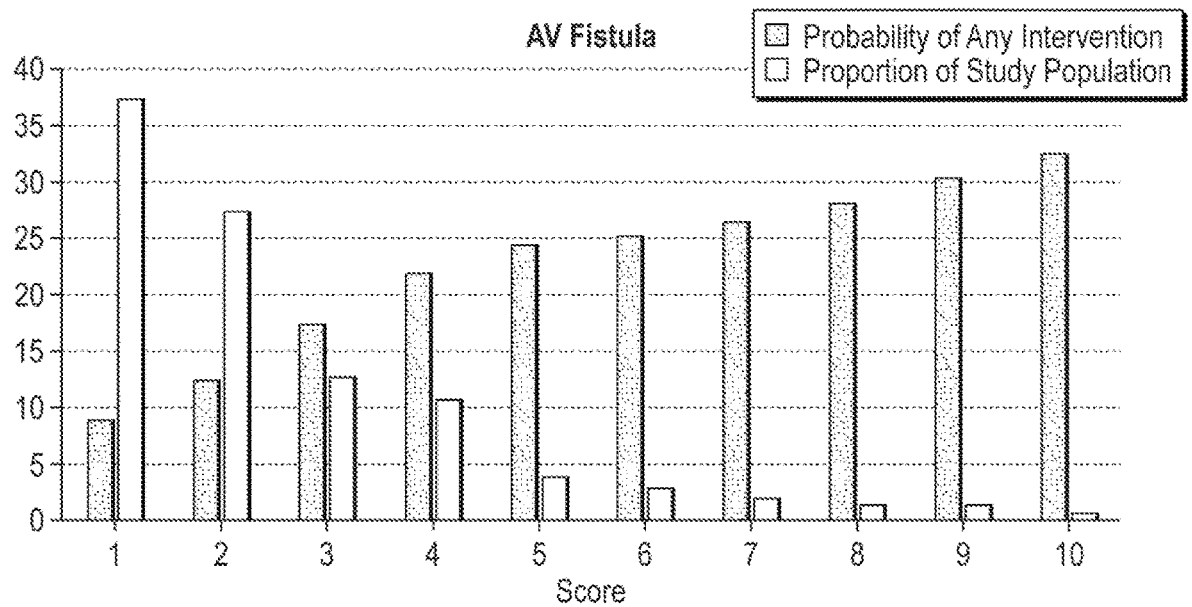
FIG. 5 is a chart depicting the probability of any intervention and the proportion of the study patient population by final risk score for AVF.
Figure 6:
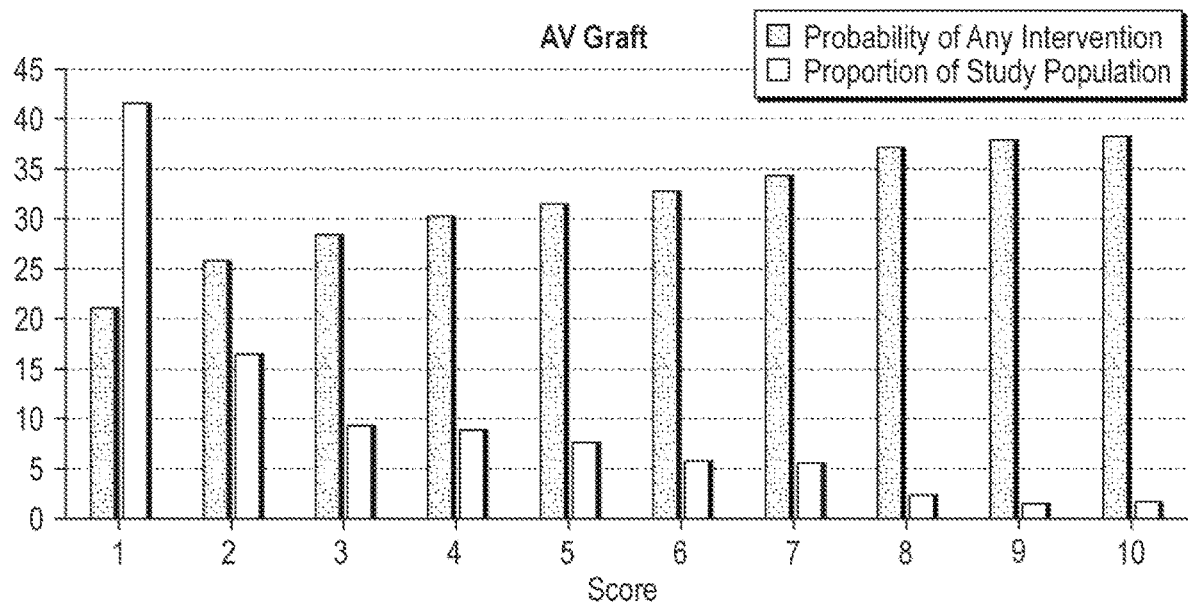
FIG. 6 is a chart depicting the probability of any intervention and the proportion of the study patient population by final risk score for AVG.

FIG. 4 is a chart illustrating the influence of vascular access location on the final risk score. In particular, this chart shows the percentage of the raw score that is associated with a given final risk score. FIG. 5 is a chart depicting the probability of any intervention and the proportion of the study patient population by final risk score for AVF, and FIG. 6 is a chart depicting the probability of any intervention and the proportion of the study patient population by final risk score for AVG.

In one application of the scoring system and method, a total of 18.9% treatments were associated with thrombosis or an intervention for AVF in the subsequent 60 days. The cumulative incidence of thrombosis was greater with higher cumulative score (see table below). Scores 1-5 were associated with a relatively low incidence of intervention (14.1% AVF, 25.7% AVG) and scores 6-10 with an increasing incidence of thrombosis or interventions in the subsequent 60 days.

| | AVF | | AVG | |
|---|---|---|---|---|
| Risk Score | % of Treatments | % of Treatments that had an Intervention | % Treatments | % of Treatments that had an Intervention |
| 1-5 | 60.2 | 14.1 | 63.4 | 25.7 |
| 6 | 15.0 | 22.1 | 12.6 | 33.1 |
| 7 | 10.6 | 25.9 | 9.5 | 36.0 |
| 8 | 7.5 | 29.3 | 7.9 | 38.7 |
| 9 | 4.8 | 31.2 | 4.6 | 41.5 |
| 10 | 1.9 | 38.2 | 2.1 | 43.2 |
| Overall | 100.0 | 18.9 | 100.0 | 29.7 |

Risk scores based upon the described scoring method successfully identified vascular accesses with low or high probability of developing access complications such as thrombosis or having an intervention to treat significant stenosis within the next 60 days. Because these scores are treatment-record based, they may be easily augmented with pertinent clinical data and automated to help guide vascular access patient care through a population management approach.

Implicit in the design is the assumption that the change between the values of a single measurement from one interval to the next may be more useful than the measurements themselves. Furthermore, a patient who presents with a persistently high VAPR and therefore is always creating an alert may be at less risk for a thrombosis event than a patient who has a VAPR slope that is changing rapidly.

In one application of the system and method disclosed herein, results for AVF (n=980,062 intervals) are shown in the tables below. The events include the first occurrence of thrombosis (n=9,814) or interventions (n=141,041). In this example, at least 4 measurements were required for each 15-day interval, participants were dropped after a gap (missing or inadequate interval), no allowance was made for prior interventions, and only the first event was used. Of course, raw and final risk score scales used herein are merely exemplary, and finer or courser scales could alternatively be used. The tables below show the results for each risk factor and the associated raw scores.

| AVF VAPR Mean | |
|---|---|
| Value | Points |
| ≤0.25 | 0 |
| >0.25 | 1 |
| >0.30 | 2 |
| >0.35 | 3 |
| >0.40 | 4 |
| >0.425 | 5 |
| >0.45 | 6 |
| >0.475 | 7 |
| >0.50 | 8 |
| >0.525 | 9 |
| >0.55 | 10 |
| >0.60 | 11 |
| >0.65 | 12 |

| AVF VAPR Slope | |
|---|---|
| Value | Points |
| −0.004-0.001 | 0 |
| >0.001 | 1 |
| >0.002 | 2 |
| >0.004 | 3 |
| >0.006 | 4 |
| >0.008 | 5 |
| >0.010 | 6 |
| >0.0125 | 7 |
| >0.015 | 8 |
| <−0.004 | 1 |
| <−0.006 | 2 |
| <−0.008 | 3 |
| <−0.010 | 4 |

| AVF VAPR Alerts | |
|---|---|
| Value | Points |
| 0 | 0 |
| 1 | 6 |
| 2 | 12 |
| 3 | 18 |
| ≥4 | 24 |

| AVF AAPR Mean | |
|---|---|
| Value | Points |
| <0.35 | 1 |
| =>0.35 to =<0.525 | 0 |
| >0.525 | 2 |
| >0.55 | 4 |
| >0.575 | 6 |
| >0.60 | 8 |

AVF
BFR < 90%

| Value | Points |
|---|---|
| 0 | 0 |
| 1 | 1 |
| =>2 | 3 |

The following table illustrates the conversion of the raw scores to the final risk score for AVF:

| Risk Score | Lower Arm AVF | Upper Arm AVF |
|---|---|---|
| 1 | 0-1 | 0-1 |
| 2 | 2-3 | 2-3 |
| 3 | 4-5 | 4-5 |
| 4 | 6-7 | 6-7 |
| 5 | 8-14 | 8-9 |
| 6 | 15-25 | 10-20 |
| 7 | 26-33 | 21-30 |
| 8 | 34-39 | 31-36 |
| 9 | 40-43 | 37-40 |
| 10 | ≥44 | ≥41 |

The following table illustrates the percentage of treatments included in each risk score and the percentage of 60-day intervals that have an intervention:

AVF

| Risk Score | % of Treatments | % of 60 Day Intervals that had an Intervention |
|---|---|---|
| 1-5 | 60.2 | 14.1 |
| 6 | 15.0 | 22.1 |
| 7 | 10.6 | 25.9 |
| 8 | 7.5 | 29.3 |
| 9 | 4.8 | 31.2 |
| 10 | 1.9 | 38.2 |
| Overall | 100.0 | 18.9 |

Figure 7:
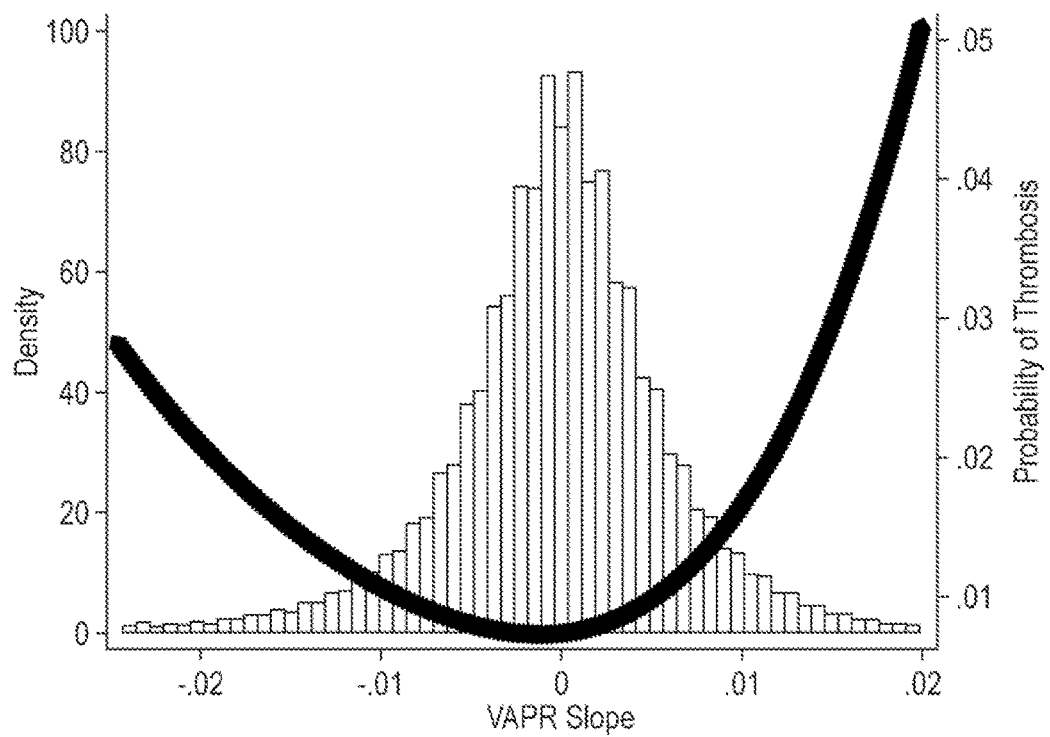
FIG. 7 is a graph showing the relative risk of complication as a function of VAPR slope for an AVF, where the greater the slope upward (right of center) or downward (left of center) indicates increasing risk.

FIG. 7 is a graph showing the relative risk of complication as a function of VAPR slope for an AVF, where the greater the slope upward (right of center) or downward (left of center) indicates increasing risk of thrombosis or an intervention.

Results for AVG (n=477,925 intervals) are shown in the tables below. The events include the first occurrence of thrombosis (n=40,176) or interventions (n=126,295). In this example, at least 4 measurements were required for each 15-day interval, participants were dropped after a gap (missing or inadequate interval), no allowance was made for prior interventions, and only the first event was used. Again, raw and final score scales used herein are merely exemplary, and finer or courser scales could alternatively be used.

AVG
VAPR Mean

| Value | Points |
|---|---|
| ≤0.40 | 0 |
| >0.40 | 1 |
| >0.45 | 2 |
| >0.50 | 3 |
| >0.55 | 4 |
| >0.60 | 5 |
| >0.65 | 6 |
| >0.70 | 7 |
| >0.80 | 8 |
| ≥0.90 | 9 |

AVG
VAPR Alerts

| Value | Points |
|---|---|
| 0 | 0 |
| 1 | 2 |
| 2 | 4 |
| 3 | 6 |
| ≥4 | 8 |

AVG
VAPR Slope

| Value | Points |
|---|---|
| -0.005-0.001 | 0 |
| >0.001 | 2 |
| >0.002 | 4 |
| >0.004 | 6 |
| >0.005 | 8 |
| >0.008 | 10 |
| >0.010 | 12 |
| >0.0125 | 14 |
| >0.015 | 16 |
| <-0.005 | 2 |
| <-0.010 | 4 |
| <-0.015 | 6 |

AVG
AAPR Mean

| Value | Points |
|---|---|
| ≤0.40 | 0 |
| >0.40 | 2 |
| >0.45 | 4 |
| >0.475 | 6 |
| >0.50 | 8 |
| >0.55 | 10 |

AVG
BFR < 90%

| Value | Points |
|---|---|
| 0 | 0 |
| 1 | 1 |
| 2 | 2 |
| ≥3 | 3 |

The following table illustrates the conversion of the raw scores to the final risk score for AVG:

| Risk Score | AVG |
| --- | --- |
| 1 | 0-3 |
| 2 | 4-5 |
| 3 | 6-8 |
| 4 | 9-10 |
| 5 | 11-14 |
| 6 | 15-17 |
| 7 | 18-20 |
| 8 | 21-24 |
| 9 | 25-29 |
| 10 | ≥30 |

The following table illustrates the percentage of treatments included in each risk score and the percentage of 60-day intervals that have an intervention:

| | AVG | |
| --- | --- | --- |
| Risk Score | % Treatments | % of 60 Day Intervals that had an Intervention |
| 1-5 | 63.4 | 25.7 |
| 6 | 12.6 | 33.1 |
| 7 | 9.5 | 36.0 |
| 8 | 7.9 | 38.7 |
| 9 | 4.6 | 41.5 |
| 10 | 2.1 | 43.2 |
| Overall | 100.0 | 29.7 |

A similar scoring system and method can be envisioned for other medical surveillance systems including a scoring algorithm designed to indicate the potential risk for a hemodialysis patient to have a hypotensive episode during a hemodialysis treatment.

Figure 8:
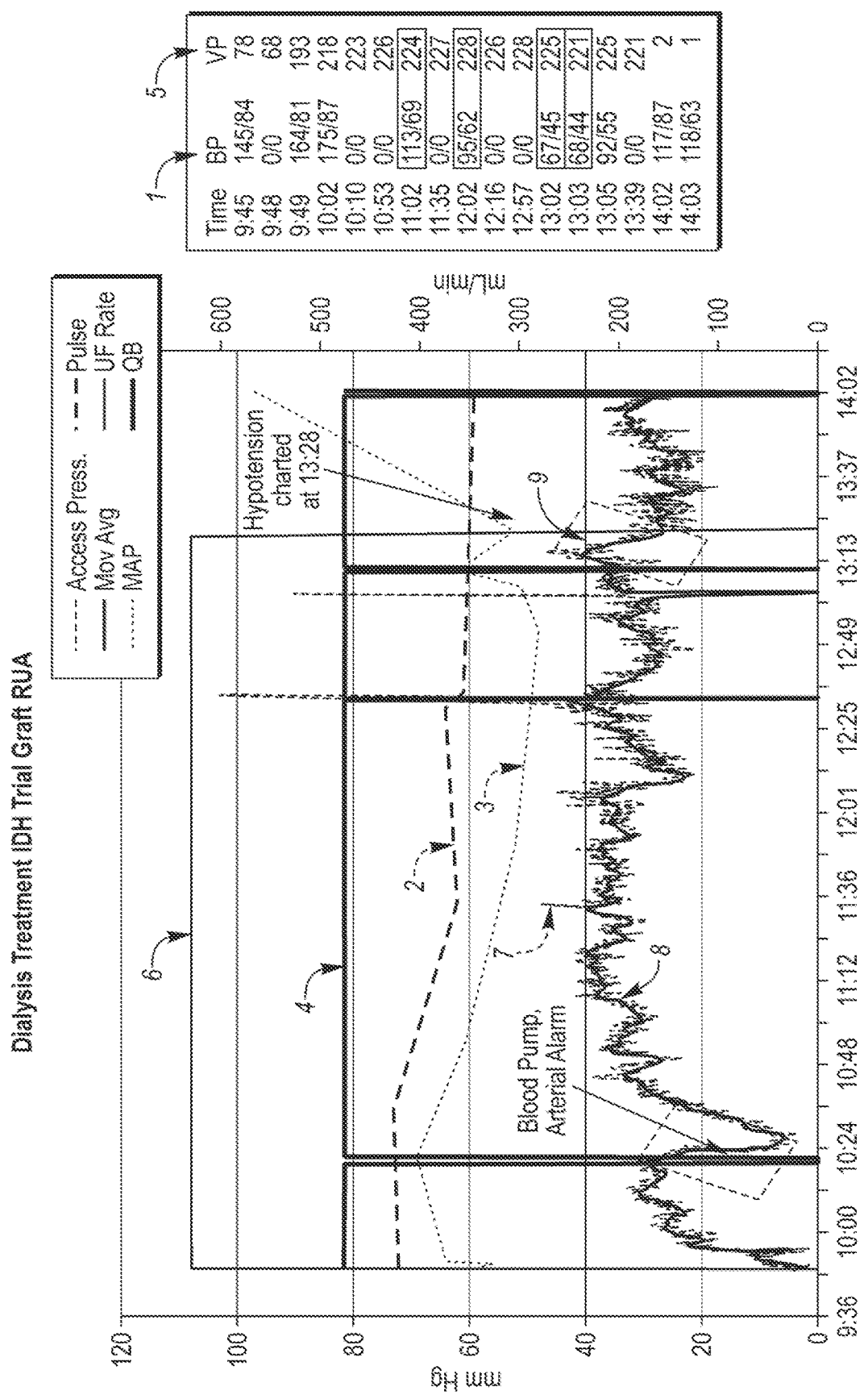
FIG. 8 shows data that can obtained during a patient's hemodialysis treatment and parameters can be continuously calculated during the hemodialysis treatment that can be included in the scoring to determine the risk of a hypotensive event during hemodialysis.

As an example of another scoring application, FIG. 8 shows data that can obtained during a patient's hemodialysis treatment which includes periodic blood pressure measurements BP (1), systolic pressure, diastolic pressure, pulse rate (2) and mean arterial pressure (3). Other important parameters recorded during hemodialysis include blood flow rate (4), venous return pressure VP (5), negative arterial pressure created by the blood pump, ultrafiltration rate (6), change in the relative circulating blood volume, time on dialysis, and blood oxygen saturation.

Several parameters can be continuously calculated during the hemodialysis treatment including the rate of change in the circulating blood volume, the blood pressure in the patient's dialysis access site (VAPR), referred to as access pressure (7), the moving average of access pressure (8) and the rate of change (slope) of the access pressure, where the shaded box (9) shows rapid decrease in slope of the access pressure that correlates with a documented hypotensive episode.

Other factors from the patient's medical history can be included in the scoring to determine the risk of a hypotensive event during hemodialysis. Patient history parameters include the total number previous hypotensive events during hemodialysis, the date of the last hypotensive event, the frequency of hypotensive events during hemodialysis, patient medications and any specific symptoms of cardiovascular disease. The patient's medical history can be given an overall score or individual scores that can accessed by the dialysis computer monitoring the patient in real time during the hemodialysis treatment.

Figure 9:
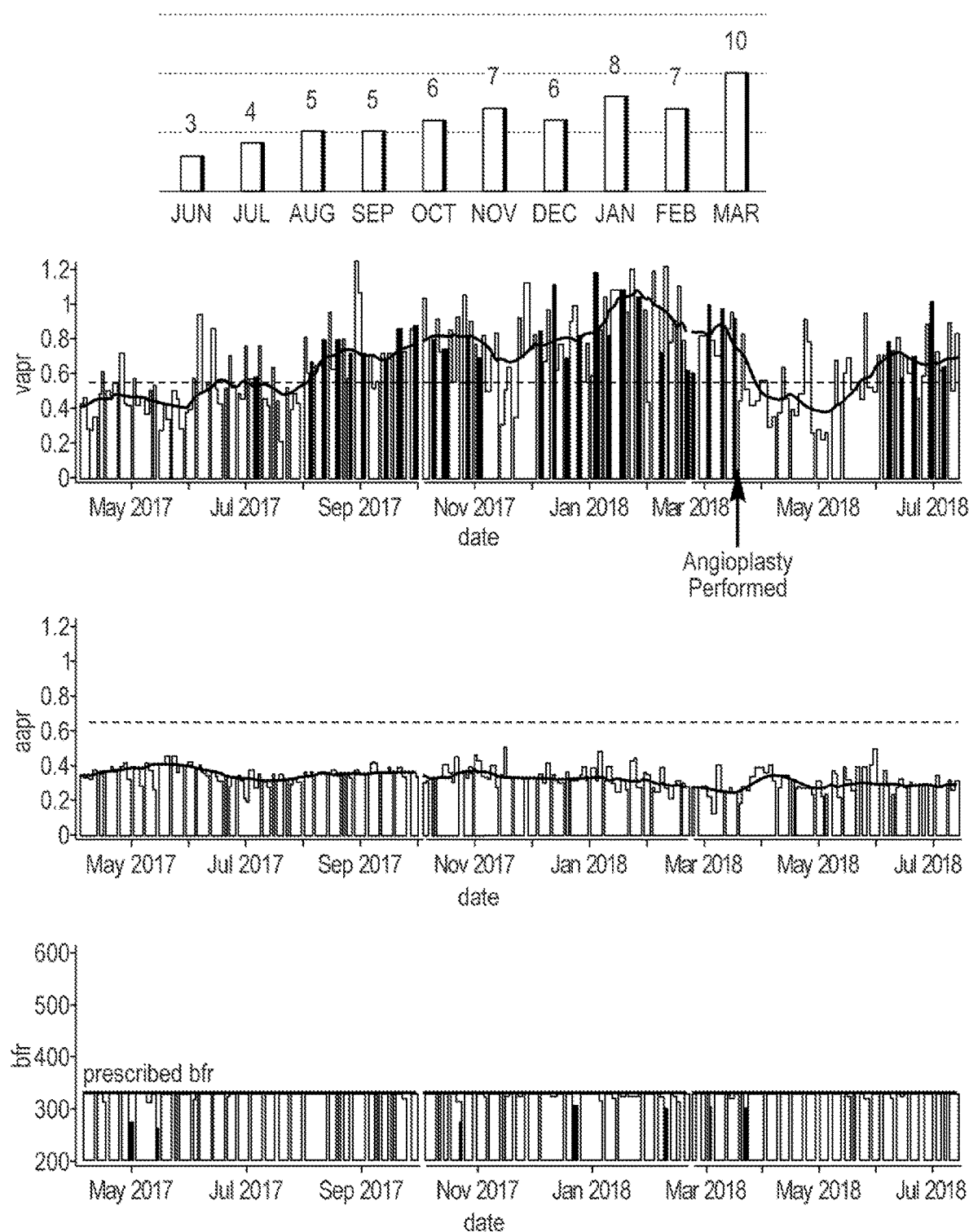
FIG. 9 depicts an example of an actual patient's AAPR, VAPR, and blood flow results showing the score each month over ten months.

FIG. 9 depicts an example of an actual patient's vascular access pressure and blood flow results showing the vascular access score over time. The top bar graph is the calculated score at the end of each month. The next lower graph is the VAPR over time, where the vertical bars represent the venous intra-access pressure calculated for each session. The dotted horizontal line is the high-pressure threshold, the darker vertical lines are calculated venous alerts, and the solid trace spanning the date axis is the running average of the venous intra-access pressure. The issues illustrated for VAPR are an upward and then a downward slope, a high average pressure, and a lot of alerts (darker vertical lines). The next graph below is AAPR, with the vertical lines indicating the calculated arterial intra-access pressure for each session. The downward slope of AAPR is indicative of growing problems. The bottom graph is hemodialysis blood flow rate (BFR) over time. The horizontal line is the prescribed blood flow, the lighter vertical lines are the average blood flow for each session, and the darker vertical lines indicate that that session did not achieve at least 90% of prescribed blood flow. The fact that an angioplasty was performed is evidence that there was a significant stenosis to correct.

Another application of the scoring method in vascular access care is to monitor catheters for changes in multiple characteristics, which can decrease the effectiveness of the hemodialysis session. For example, changes in the normalized arterial and/or venous pressure, changes in the blood viscosity (Hct) and other indicators may signal impediments or changes to the ability of blood to flow through the catheter. A reduction in blood flow through a catheter might indicate the growth of a fibrin sheath over time. This will impact the success of hemodialysis treatment and may result in the catheter requiring additional medical procedures to maintain proper function.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A method for determining risk of an adverse event associated with a vascular access, the method comprising:
   receiving hemodialysis treatment data associated with the vascular access from a plurality of hemodialysis treatment sessions over a time period in a database;
   with a microprocessor in communication with the database, repeatedly analyzing the hemodialysis treatment data over the time period to calculate values of a plurality of risk factors for the vascular access; and
   using the microprocessor, determining raw scores for each risk factor based on its values over the time period and summing the raw scores for the plurality of risk factors to determine a cumulative raw score indicative of a level of risk of an adverse event associated with the vascular access.

2. The method of claim 1, further comprising correlating the cumulative raw score with a final risk score, wherein a higher final risk score is associated with a higher probability of an adverse event for the vascular access.

3. The method of claim 1, further comprising prioritizing the vascular access for risk of an adverse event compared with a plurality of other vascular accesses within a hemodialysis patient population.

4. The method of claim 1, wherein the adverse event includes at least one of thrombosis or intervention required for the vascular access.

5. The method of claim 1, wherein the hemodialysis treatment data includes venous access pressure (VAP), arterial access pressure (AAP), and mean arterial pressure (MAP), and the method further includes repeatedly calculating a venous access pressure ratio (VAPR) over the time period by normalizing VAP with respect MAP and calculating an arterial access pressure ratio (AAPR) by normalizing AAP with respect to MAP.

6. The method of claim 1, wherein the plurality of risk factors includes a number of VAPR and AAPR alerts for exceeding a threshold pressure level over the time period.

7. The method of claim 1, wherein the plurality of risk factors includes an average VAPR over the time period.

8. The method of claim 1, wherein the plurality of risk factors includes an average AAPR over the time period.

9. The method of claim 1, wherein the plurality of risk factors includes a slope of VAPR over the time period.

10. The method of claim 1, wherein the plurality of risk factors includes a number of hemodialysis treatment sessions that do not achieve at least 90% of a prescribed blood flow rate.

11. The method of claim 1, wherein the cumulative raw score is categorized based on a type and location of the vascular access.

12. A method for determining risk of an adverse event associated with a vascular access, the method comprising:
with a microprocessor, repeatedly analyzing hemodialysis treatment data associated with the vascular access from a plurality of hemodialysis treatment sessions over a time period to calculate values of a plurality of risk factors for the vascular access relating to VAPR, AAPR and blood flow rate; and
using the microprocessor, determining raw scores for each risk factor based on its values over the time period, summing the raw scores for the plurality of risk factors to determine a cumulative raw score, and correlating the cumulative raw score with a final risk score indicative of a probability of an adverse event associated with the vascular access.

13. The method of claim 12, further comprising prioritizing the vascular access for risk of an adverse event compared with a plurality of other vascular accesses within a hemodialysis patient population.

14. The method of claim 12, wherein the adverse event includes at least one of thrombosis or intervention required for the vascular access.

15. The method of claim 12, wherein the plurality of risk factors includes a number of VAPR and AAPR alerts for exceeding a threshold pressure level over the time period.

16. The method of claim 12, wherein the plurality of risk factors includes an average VAPR and average AAPR over the time period.

17. The method of claim 12, wherein the plurality of risk factors includes a slope of VAPR over the time period.

18. The method of claim 12, wherein the plurality of risk factors includes a number of hemodialysis treatments that do not achieve at least 90% of a prescribed blood flow rate.

19. The method of claim 12, wherein the cumulative raw score is categorized based on a type and location of the vascular access.

20. A method for determining risk of thrombosis or a required intervention associated with a vascular access, the method comprising:
receiving hemodialysis treatment data associated with the vascular access from a plurality of hemodialysis treatment sessions over a time period in a database;
with a microprocessor in communication with the database, repeatedly analyzing the hemodialysis treatment data over the time period to calculate values of a plurality of risk factors for the vascular access relating to VAPR, AAPR and blood flow rate;
with the microprocessor, determining raw scores for each risk factor based on its values over the time period, wherein the values include averages, slopes, and number of alerts, summing the raw scores for the plurality of risk factors to determine a cumulative raw score, and correlating the cumulative raw score with a final risk score indicative of a probability of thrombosis or a required intervention associated with the vascular access; and
using the microprocessor, analyzing the final risk score of the vascular access over the time period for prioritizing the vascular access for risk of thrombosis or a required intervention compared with a plurality of other vascular accesses within a hemodialysis patient population.

* * * * *